(12) United States Patent
Reynolds, II et al.

(10) Patent No.: US 8,028,704 B2
(45) Date of Patent: Oct. 4, 2011

(54) ENDOSCOPIC BITE BLOCK FOR USE WITH CANNULA

(75) Inventors: Donald L. Reynolds, II, West Chester, OH (US); Randy R. Stephens, Fairfield, OH (US); Richard W. Flaker, Fairfield, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 116 days.

(21) Appl. No.: 12/132,081

(22) Filed: Jun. 3, 2008

(65) Prior Publication Data

US 2008/0295849 A1 Dec. 4, 2008

Related U.S. Application Data

(60) Provisional application No. 60/941,707, filed on Jun. 4, 2007.

(51) Int. Cl.
*A61C 5/14* (2006.01)
(52) U.S. Cl. ...................................................... 128/859
(58) Field of Classification Search .................. 128/859, 128/861, 862, 200.26, 200.27, 206.21
See application file for complete search history.

(56) References Cited

U.S. PATENT DOCUMENTS

| | | | |
|---|---|---|---|
| 39,175 A | 7/1863 | Scholfield | |
| 803,475 A | 10/1905 | Dennis | |
| 2,127,215 A | 8/1938 | Gwathmey | |
| 3,756,244 A * | 9/1973 | Kinnear et al. | 128/207.14 |
| 3,771,514 A | 11/1973 | Huffman et al. | |
| 3,774,616 A | 11/1973 | White et al. | |
| 4,270,531 A | 6/1981 | Blachly et al. | |
| 4,425,911 A | 1/1984 | Luomanen | |
| 4,495,945 A | 1/1985 | Liegner | |
| 4,679,573 A | 7/1987 | Parnoff | |
| 4,793,327 A | 12/1988 | Frankel | |
| 4,944,313 A | 7/1990 | Katz et al. | |
| 4,992,046 A | 2/1991 | Sharp | |
| 5,069,668 A | 12/1991 | Boydman | |
| D329,901 S | 9/1992 | Jackson | |
| 5,174,284 A | 12/1992 | Jackson | |
| 5,273,032 A | 12/1993 | Borody | |
| 5,308,317 A | 5/1994 | Ferguson et al. | |
| 5,318,017 A | 6/1994 | Ellison | |
| 5,368,562 A | 11/1994 | Blomquist et al. | |
| 5,386,821 A | 2/1995 | Poterack | |
| 5,413,095 A | 5/1995 | Weaver | |

(Continued)

FOREIGN PATENT DOCUMENTS

DE 3543931 6/1987

(Continued)

OTHER PUBLICATIONS

Oxyguard D® Bite Block With Oxygen, http/www.usendoscopy.com/oxy.htm, pp. 1-2, May 2, 2002.

(Continued)

*Primary Examiner* — Patricia Bianco
*Assistant Examiner* — Camtu Nguyen
(74) *Attorney, Agent, or Firm* — Verne E. Kreger, Jr.

(57) ABSTRACT

A bite block that is inserted into a patient's mouth during an endoscopic diagnostic or surgical procedure that has a channel for receiving an endoscope or other surgical instrument through the patient's mouth and additional channels transmitting a gas to the patient and transmitting expired gas from the patient.

17 Claims, 5 Drawing Sheets

U.S. PATENT DOCUMENTS

| | | | |
|---|---|---|---|
| 5,421,327 A | 6/1995 | Flynn et al. | |
| 5,431,158 A | 7/1995 | Tirotta | |
| 5,513,627 A | 5/1996 | Flam | |
| 5,513,634 A | 5/1996 | Jackson | |
| 5,590,643 A | 1/1997 | Flam | |
| 5,620,408 A | 4/1997 | Vennes et al. | |
| 5,649,540 A | 7/1997 | Alvarez et al. | |
| 5,655,519 A | 8/1997 | Alfery | |
| 5,699,787 A | 12/1997 | Thompson | |
| 5,800,387 A | 9/1998 | Duffy et al. | |
| 5,846,182 A | 12/1998 | Wolcott | |
| 5,857,461 A | 1/1999 | Levitsky et al. | |
| 5,957,885 A | 9/1999 | Bollish et al. | |
| 6,257,238 B1 | 7/2001 | Meah | |
| 6,379,312 B2 * | 4/2002 | O'Toole | 600/529 |
| 6,386,199 B1 | 5/2002 | Alfery | |
| 6,494,209 B2 | 12/2002 | Kulick | |
| 6,517,549 B1 | 2/2003 | Dennis | |
| 6,533,761 B2 | 3/2003 | Bertoch | |
| 6,743,017 B2 * | 6/2004 | O'Neill | 433/140 |
| 6,926,005 B1 | 8/2005 | Colman et al. | |
| 2001/0031929 A1 | 10/2001 | O'Toole | |
| 2004/0129272 A1 | 7/2004 | Ganesh et al. | |
| 2004/0129273 A1 | 7/2004 | Hickle | |
| 2005/0081861 A1 | 4/2005 | Nasir | |
| 2005/0267415 A1 | 12/2005 | Jacques | |
| 2006/0042637 A1 | 3/2006 | Martin et al. | |

FOREIGN PATENT DOCUMENTS

| | | |
|---|---|---|
| GB | 2170106 A | 7/1986 |
| GB | 2173105 A | 10/1986 |
| GB | 2364644 A | 2/2002 |
| WO | WO 9508356 A2 | 3/1995 |
| WO | WO 2003/020340 A2 | 3/2003 |
| WO | WO 2004/030723 A2 | 4/2004 |
| WO | WO 2004/103199 A2 | 12/2004 |
| WO | WO 2005/016142 A1 | 2/2005 |

OTHER PUBLICATIONS

International Search Report dated Oct. 6, 2008 for the corresponding PCT application PCT/US2008/065630.

* cited by examiner

ENDOSCOPIC BITE BLOCK FOR USE WITH CANNULA

CROSS REFERENCE TO RELATED APPLICATIONS

The present application claims the priority benefit of U.S. provisional patent application Ser. No. 60/941,707, filed on Jun. 4, 2007, the contents of which are incorporated by reference in their entirety herein.

FIELD OF THE INVENTION

The present invention relates, in general, to bite blocks for use in endoscopic surgical procedures, and in particular, to endoscopic bite blocks for use in procedures involving sedation and analgesia systems.

BACKGROUND OF THE INVENTION

During some medical procedures, specifically endoscopic procedures, it is necessary to insert medical instruments, such as an endoscope, into the mouth and down the trachea or esophagus of a patient. It is common to use in such procedures a bite block or mouthguard to protect both the patient's mouth from the endoscope and the endoscope from the patient's mouth. The bite block or mouthguard essentially maintains the patient's mouth in the open position, providing an opening through which the endoscope can be passed, and prevents the patient from biting down on the endoscopic instruments, which are often quite expensive. Bite blocks capable of such function are generally known in the art; bite blocks designed for use with sedation and analgesia delivery and patient monitoring systems, however, are not.

In order to increase comfort and reduce patient resistance to the advancing of the scope, patients are often sedated during endoscopic procedures. In the case when the particular sedation drugs are respiratory depressants, there exist certain well-known risks related to patient respiration, including hypoventilation, oxygen desaturation, and apnea. In order to mitigate these risks, supplementary oxygen and respiratory monitoring are often utilized. Both the administration of supplementary oxygen and the sampling of respiratory gasses for monitoring require access to the patient's respiratory orifices, usually accomplished via oral-nasal cannula. Difficulties sometimes arise, however, when simultaneously managing the scope, delivering supplementary oxygen, and sampling respiratory gasses via the oral cavity. If the oral cavity could be reserved for exclusive use by the endoscope and the nasal passages used for oxygen delivery and respiratory sampling, the difficulty would be greatly reduced. Unfortunately, this method would require that the patient inhale and exhale only through the nasal passages for the duration of the procedure; in a real-world scenario, however, this is not the case.

It is therefore desirable for endoscopic procedures that require sedation to allow maneuvering of an endoscope into the oral cavity simultaneous with oral and nasal oxygen delivery and expired gas sampling. It indeed requires little imagination to see that accommodating all three activities simultaneously through the oral cavity with instruments not designed to be used together would prove troublesome. It follows that, as the endoscopy is the main focus of the procedure, it would take priority in use of the oral cavity over the other two functions. While focusing on the endoscope, an oral-nasal cannula is rather easily bumped and relocated during the maneuvering of the scope, leaving its oral ports situated too far from the oral cavity and occasionally causing bruising internal to the nasal passages. The consequence is decreased effectiveness in the administration of supplementary oxygen and sampling of respiratory gasses, which in turn may compromise patient safety.

In addition, in current practice, some doctors use a finger to help guide the endoscope into the mouth and down the trachea or esophagus of the patient. To do so, a doctor may stick a finger inside a patient's mouth, outside of the bite block, in order to control the endoscope near the opening to the trachea or esophagus. This requires that the finger be inserted at least to the depth of the end of the bite block, which may cause the bite block to move around. This adds to the risk that, during all of the jostling of the bite block associated with the maneuvering of the endoscope and insertion of a finger, the oral ports of the cannula may be unintentionally relocated away from the oral cavity.

It is therefore the object of the present invention to provide a bite block with means for locating and protecting the oral ports of an oral-nasal cannula and to facilitate simultaneous use of the oral cavity for an endoscopic diagnostic or surgical procedure, supplemental oxygen delivery, and respiratory sampling.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
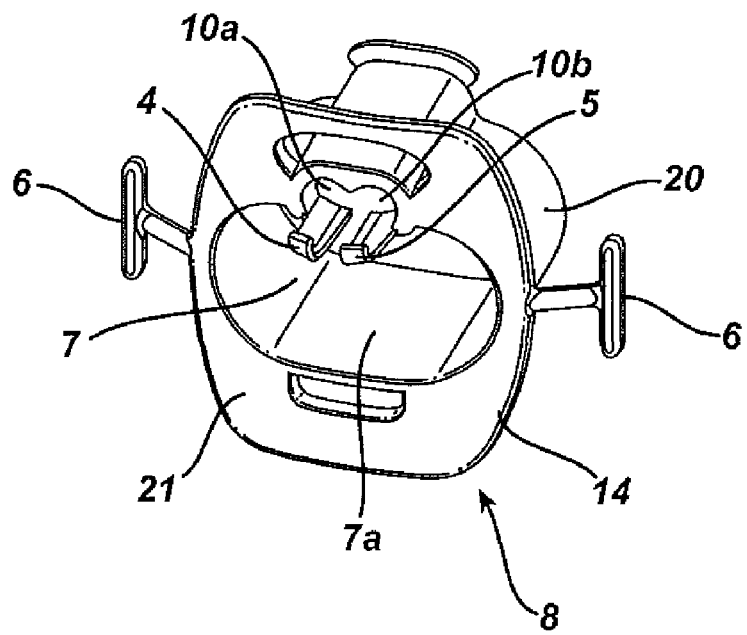
FIG. 1 is a front perspective view of a bite block in accordance with the present invention.
Figure 2:
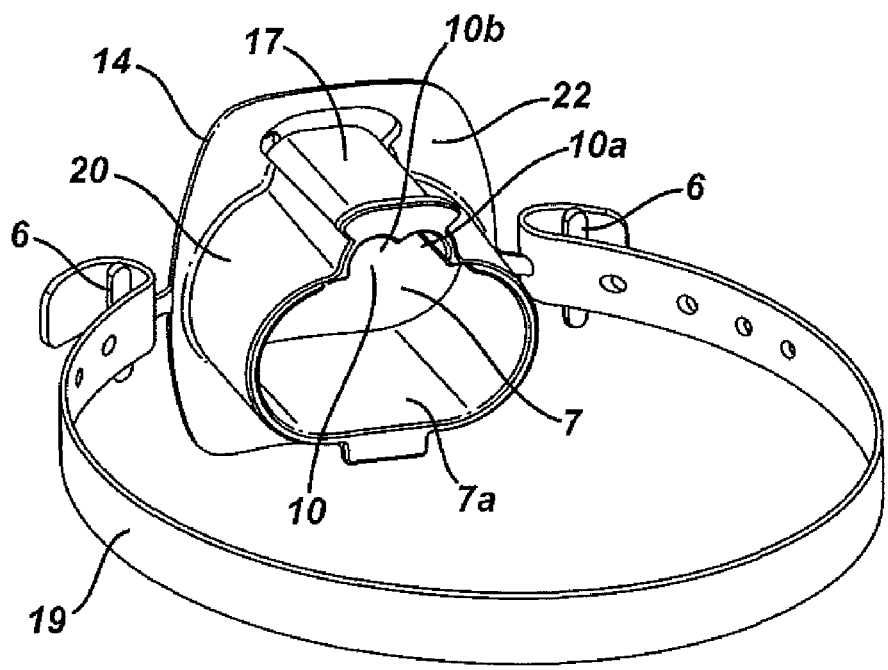
FIG. 2 is back perspective view of a bite block in accordance with the present invention.
Figure 5:
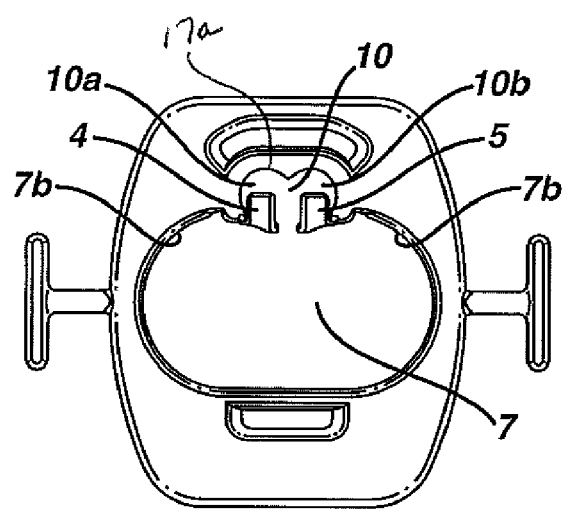
FIG. 5 is a front view of a bite block in accordance with the present invention.

Referring to FIG. 1 and FIG. 2, the bite block 8 of the present invention consists of a generally elliptical cylindrical main body 20, having a proximal end, which sits outside of a patient's mouth, and a distal end, which sits inside a patient's mouth. Main body 20 surrounds main oral passage lumen or channel 7, which is sized to allow for passage of an endoscope and ventilation of the patient. Oral passage 7 is defined by a lower surface 7a and an upper surface 7b (FIG. 5). Upper surface 7b further defines an opening for internal gas channel or lumen 10 (FIG. 5). Integral to the proximal end of main body 20 is flange 14, which sits outside of a patient's lips and serves both to locate bite block 8 relative to the patient's mouth and protect the patient's lips and teeth from an endoscope. Flange 14 is integral to main body 20 at distal surface 22. Attached at each side of flange 14 is strap attachment wing 6 for strap 19 that goes around the patient's head and helps secure bite block 8.

Figure 3:
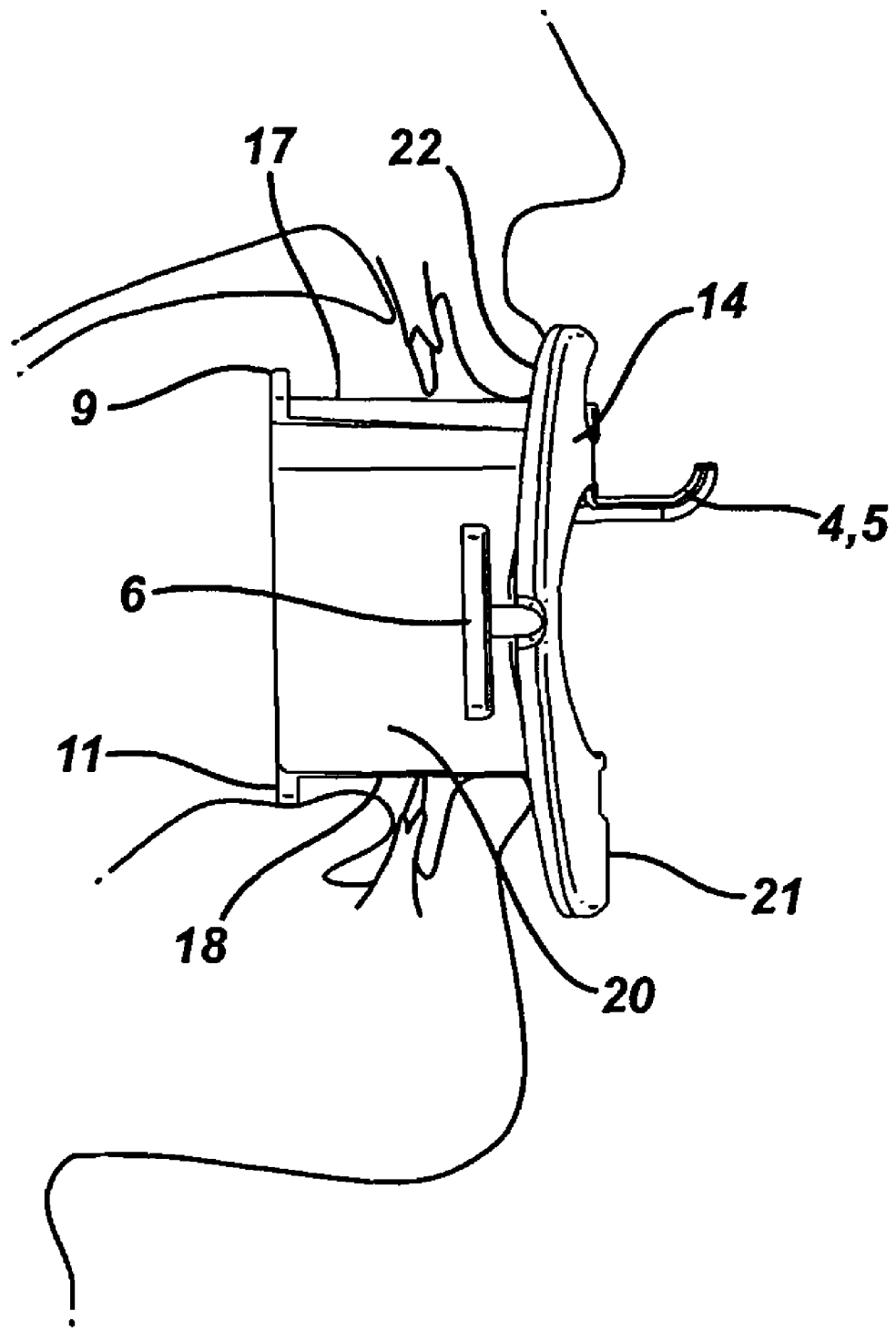
FIG. 3 is a side view of a bite block in accordance with the present invention, shown in a section view of a patient's mouth.

Referring to FIG. 3, extending from the proximal to distal end of main body 20, are a raised top surface 17 and bottom surface 18 for seating patient's upper teeth and lower teeth, respectively. Located at the distal end of top surface 17 is upper protruding retention feature 9, protruding up generally perpendicular to top surface 17. Upper protruding retention feature 9 serves as a stop to keep bite block 8 from being expelled from a patient's mouth by requiring the mouth (or more particularly, the teeth) to be opened wide enough to get around retention feature 9. Similarly, on bottom surface 18 is lower protruding retention feature 11 serving the same purpose.

Figure 4:
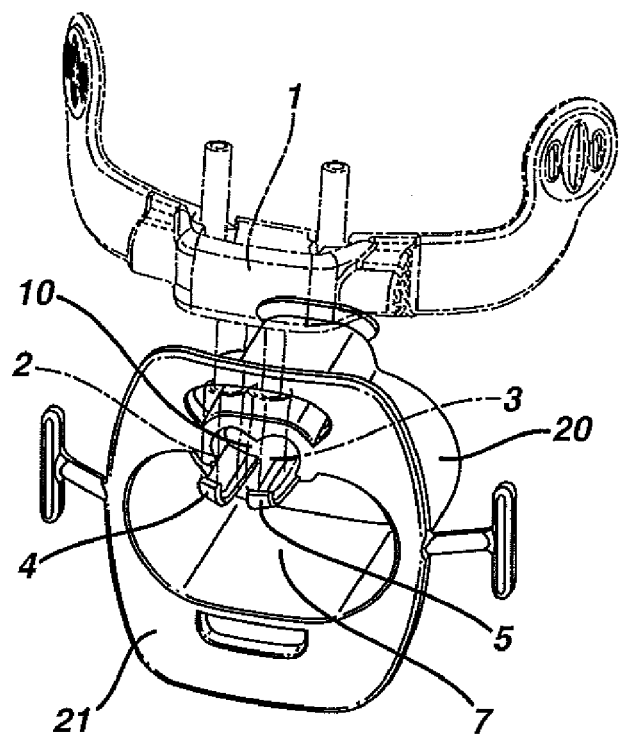
FIG. 4 is a perspective view of a bite block in accordance with the present invention and a typical oral-nasal cannula, shown together, interfaced as they would be used during a procedure.
Figure 6:
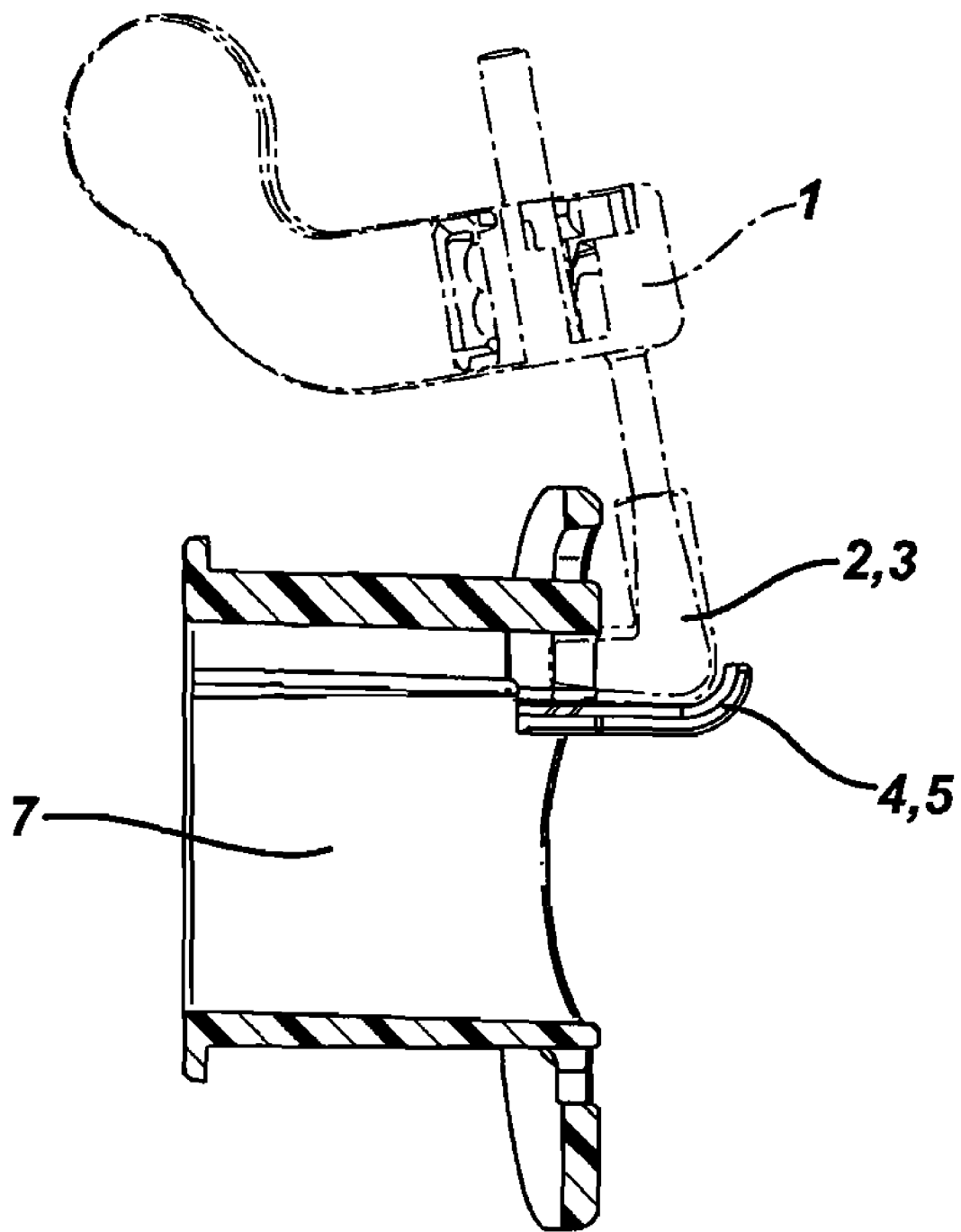
FIG. 6 is a side section view of a bite block in accordance with the present invention and a typical oral-nasal cannula, shown together, interfaced as they would be used during a procedure.

Referring also now to FIGS. 4 and 6, some features of the present invention are intended to interface with an oral-nasal cannula 1, generally known in the art, with oxygen outlet port 2 and $CO_2$ sampling inlet port 3. A representative oral-nasal cannula is described in pending application US-2006-0042636, the contents of which are incorporated by reference in its entirety herein. Oxygen outlet port 2 is the end of the oxygen delivery fluid line that delivers oxygen into the patient's oral cavity, and $CO_2$ sampling inlet port 3 is the end of the fluid line of a capnometry or capnography system through which expired $CO_2$ enters from a patient's oral cavity. Oxygen outlet port 2 and $CO_2$ sampling inlet port 3 consist of tubular extensions downward from the main body of cannula 1, bent in a generally perpendicular fashion towards the patient's mouth. In the absence of a bite block, the openings of oxygen outlet port 2 and $CO_2$ sampling inlet port 3 would rest at the opening to the oral cavity.

Referring also now to FIG. 5, internal to main body 20, and extending from the proximal end to the distal end of main body 20, and adjacent to main oral passage 7, is internal gas channel 10. Internal gas channel 10 consists of two parallel adjacently-connected sub-channels 10a and 10b, each of semi-circular cross section, which define a top surface 17a. Internal gas channel 10 occupies the area under raised surface 17. Internal gas channel 10 allows the exchange of gas from the proximal end (external to the patient's mouth) of bite block 8 to the distal end (internal to the patient's mouth), and vice versa, without using a significant amount of the cross-sectional area of main oral passage 7, which is reserved for use by the endoscope. As seen in FIG. 4, internal gas channel 10 provides a path via one sub-channel 10a (for example) for oxygen to flow from oxygen outlet port 2 of an oral-nasal cannula 1 into the patient's mouth and, via the other sub-channel 10b (for example), for $CO_2$ to flow from the patient's mouth into $CO_2$ sampling inlet port 3 of cannula 1. The sub-channels 10a, 10b of internal gas channel 10 can be used interchangeably for either oxygen or $CO_2$, depending on where the respective ports are located on cannula 1.

Oxygen port support 4 and $CO_2$ port support 5 protrude from proximal surface 21 of flange 14, and proximal from internal gas channel 10. Oxygen port support 4 and $CO_2$ port support 5, each consist of a generally flat extension extending from proximal surface 21, and generally symmetrical with respect to the vertical plane aligned longitudinally along main body 20. From their points of attachment located on the side away from the center axis of main body 20, oxygen port support 4 and $CO_2$ port support 5 slope slightly downward toward the center of main oral passage 7. Oxygen port support 4 and $CO_2$ port support 5 also extend in the distal direction for approximately the thickness of flange 14, as best seen in FIGS. 1 and 6, partially separating main oral passage 7 and internal gas channel 10. This arrangement is designed to allow the ends of oxygen outlet port 2 and $CO_2$ sampling inlet port 3 of cannula 1 to rest inside internal gas channel 10, as shown in FIG. 6. Oxygen port support 4 and $CO_2$ port support 5 each terminate on their proximal ends in an upward-curving quarter-circular shaped feature, which provides a means for more securely locating near the oral cavity oxygen outlet port 2 of the oxygen delivery system and $CO_2$ sampling inlet port 3 of a capnometry or capnography system. Oxygen port support 4 and $CO_2$ port support 5 are intended to provide a means for protecting the location of oxygen outlet port 2 and $CO_2$ sampling inlet port 3 against jostling from the movement of the scope. The terms "oxygen port support" and "$CO_2$ port support" are used only illustratively in this description; since the supports are generally symmetrical, they could be used interchangeably, depending on which side of cannula 1 each port was located.

Figure 7:
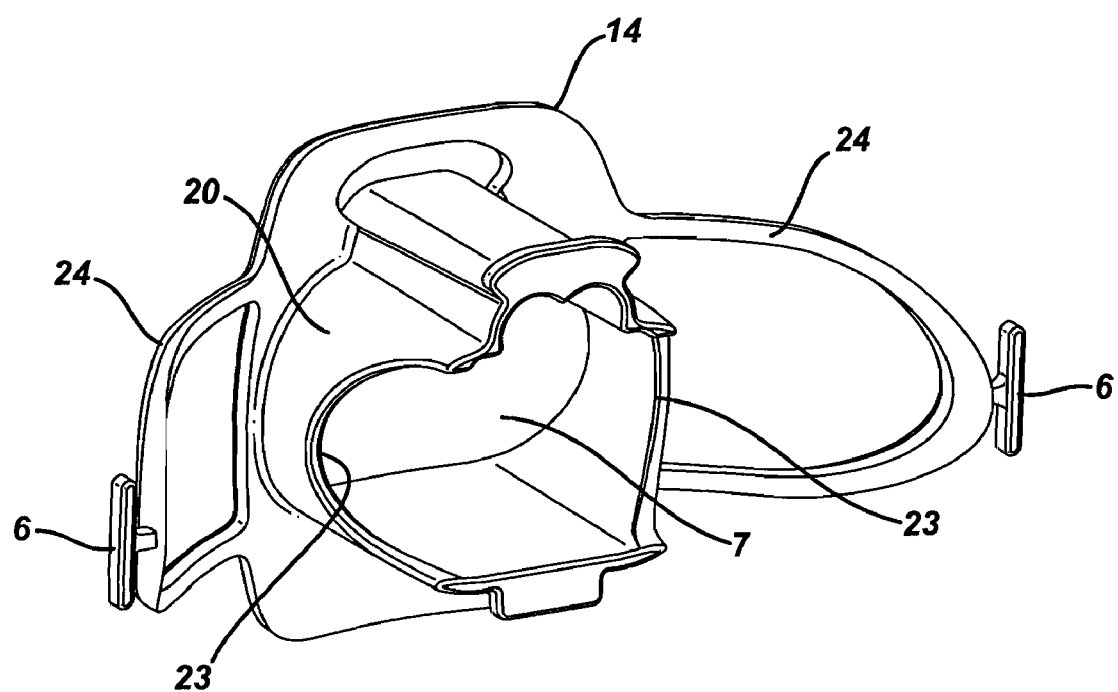
FIG. 7 is a rear perspective view of an alternate embodiment of the present invention.

An alternate embodiment of the present invention, shown in FIG. 7, adds additional functionality by allowing a doctor to insert a finger a short distance into the patient's mouth to help guide the endoscope down into the trachea or esophagus, while again preventing excessive jostling of bite block 8 and cannula 1. In the alternate embodiment, main body 20 has curved cutouts 23 on its distal end, on both of its sides. In addition, integral to flange 14, and extending out on both of its sides, are strap attachment wing extenders 24, each consisting of a thin arced, 'c'-shaped protrusion, defining an opening. Cutouts 23 and strap attachment wing extenders 24 are sized and located such that a finger may be inserted through the open side of the 'c' of strap attachment wing extender 24 and past cutout 23 into the patient's mouth. Strap attachment wing extenders 24 also locate the strap attachment wings 6 such that the strap is not in the way of a finger. In this manner, a doctor would be able to easily guide an endoscope with a finger without using any of the cross sectional area of main oral passage 7, and without too much jostling of bite block 8 and cannula 1.

While preferred embodiments of the present invention have been shown and described herein, it will be obvious to those skilled in the art that such embodiments are provided by way of example only. In addition, it should be understood that every structure described above has a function and such structure can be referred to as a means for performing that function. Numerous variations, changes, and substitutions will now occur to those skilled in the art without departing from the invention. Accordingly, it is intended that the invention be limited only by the spirit and scope of the appended claims.

We claim:

1. An endoscopy bite block defining a front flange to overlap a patient's mouth and an opening configured to be received between the patient's lower and upper jaw and sized to provide access to the patient's oral cavity, the opening defines i) a first channel member extending into the patient's oral cavity and having a proximal end and a distal end, wherein the first channel member comprises a lower surface and an upper surface and the upper surface defines, ii) a second channel member coincident with the proximal end and the distal end and further defining a third surface substantially parallel to the lower surface and superior thereto and iii) a first support member positioned intermediate the first channel and the second channel and extending proximally from the front flange.

2. The bite block of claim 1, wherein the first channel member is oval-shaped.

3. The bite block of claim 1, wherein the second channel member comprises a first arcuate sub-channel and a second arcuate sub-channel immediately adjacent to the first arcuate sub-channel.

4. The bite block of claim 1, wherein the second channel member is sized to accommodate a tube for delivering a gas to the patient or monitoring the patient's exhalation.

5. The bite block of claim 1, wherein a second support member extends proximally from the front flange.

6. The bite block of claim 1 further comprising a second opening adjacent the first channel sized to accommodate a finger.

7. The bite block of claim 6, wherein the first channel comprises lateral cut-out extending from the distal end and toward the proximal end.

8. The bite block of claim 1, wherein the second channel member is sized to accommodate a tube for delivery a gas to the patient and a tube for monitoring the patient's exhalation.

9. A kit for performing an endoscopic procedure comprising:
   a. A bite block defining a front flange to overlap a patient's mouth and an opening configured to be received between the patient's lower and upper jaw and for communicating with the patient's oral cavity, the opening defines i) a first channel member extending into the patient's oral cavity and having a proximal end and a distal end, wherein the first channel member comprises a lower surface and an upper surface, ii) a second channel member coincident with the proximal end and the distal end and further defining a third surface substantially parallel to the lower surface and superior thereto, a first support member positioned intermediate the first channel and the second channel and extending proximally from the front flange; and
   b. a cannula having a first port for receiving a first gas, a second port for transmitting a second gas, a third port for delivering the first gas to the patient and a fourth port for receiving the second gas from the patient, wherein the second channel member is sized to accommodate the third and fourth ports.

10. An endoscopy bite block defining a front flange to overlap a patient's mouth and an opening configured to be received between the patient's lower and upper jaw and sized to provide access to the patient's oral cavity, the opening defines i) a first channel member extending into the patient's oral cavity and having a proximal end and a distal end, wherein the first channel member comprises a lower surface and an upper surface and the upper surface defines, ii) a second channel member defining a third surface substantially parallel to the lower surface and superior thereto and iii) a first support member positioned intermediate the first channel and the second channel and extending proximally from the front flange.

11. The bite block of claim 10, wherein the second channel member is sized to accommodate a tube for delivery a gas to the patient and a tube for monitoring the patient's exhalation.

12. The bite block of claim 10, wherein the first channel member is oval-shaped.

13. The bite block of claim 10, wherein the second channel member comprises a first arcuate sub-channel and a second arcuate sub-channel immediately adjacent to the first arcuate sub-channel.

14. The bite block of claim 10, wherein a second support member extends proximally from the front flange.

15. The bite block of claim 10 further comprising a second opening adjacent the first channel sized to accommodate a finger.

16. The bite block of claim 15, wherein the first channel comprises lateral cut-out extending from the distal end and toward the proximal end.

17. The bite block of claim 10, wherein the second channel member is sized to accommodate a tube for delivering a gas to the patient or monitoring the patient's exhalation.

* * * * *